(12) United States Patent
DeHart

(10) Patent No.: US 7,292,049 B2
(45) Date of Patent: Nov. 6, 2007

(54) SYSTEM AND METHOD FOR DETECTING THE DIELECTRIC CONSTANT OF CONDUCTIVE MATERIAL

(75) Inventor: Scott Alan DeHart, Eagle, ID (US)

(73) Assignee: Base line, LLC, Boise, ID (US)

( * ) Notice: Subject to any disclaimer, the term of this patent is extended or adjusted under 35 U.S.C. 154(b) by 0 days.

(21) Appl. No.: 11/163,913

(22) Filed: Nov. 3, 2005

(65) Prior Publication Data

US 2007/0103170 A1 May 10, 2007

(51) Int. Cl.
G01R 27/32 (2006.01)
B05B 12/08 (2006.01)
(52) U.S. Cl. ........................................ 324/643; 239/63
(58) Field of Classification Search ................ 324/643; 239/63
See application file for complete search history.

(56) References Cited

U.S. PATENT DOCUMENTS 5,148,985 A * 9/1992 Bancroft ...................... 239/64
6,281,801 B1 * 8/2001 Cherry et al. ................ 324/643
6,657,443 B2 * 12/2003 Anderson .................... 324/664
6,798,215 B2 9/2004 DeHart ........................ 324/640
6,831,468 B2 * 12/2004 Anderson et al. ........... 324/664

* cited by examiner

Primary Examiner—Walter Benson
Assistant Examiner—Timothy J Dole
(74) Attorney, Agent, or Firm—Technology Law Group, LLC; Robert A. Huntsman

(57) ABSTRACT

An improved system and method for providing a dielectric monitor which allows the measurement of the dielectric constant of a conductive material. The capability to accurately and efficiently measure the dielectric constant in soil allows the moisture content of the soil to be accurately determined. The preferred embodiment teaches a sensor that has the ability to compensate for some level of variable conductivity. Alternate embodiments are applicable to areas other than soil moisture measurement.

3 Claims, 3 Drawing Sheets

SYSTEM AND METHOD FOR DETECTING THE DIELECTRIC CONSTANT OF CONDUCTIVE MATERIAL

DESCRIPTION OF THE RELEVANT ART

This application expands on and builds on the technology disclosed by DeHart in U.S. Pat. No. 6,798,215.

SUMMARY OF THE INVENTION

It is the object of the present invention to provide a dielectric monitor which allows the measurement of the dielectric constant of a conductive material. The capability to measure the dielectric constant allows the moisture content of soils, where the sensor has the ability to compensate for some level of variable conductivity. The technique is also applicable to other areas beyond soil moisture measurement.

The dielectric constant of a medium can be found by measuring the propagation delay of a wave traveling through that medium. The following formula gives the relationship between propagation velocity (V) and the bulk dielectric constant (k). C is the speed of light in a vacuum.

$$V=C/k^{0.5}$$

Solving for bulk dielectric constant (k)

$$k=(C/V)^2$$

In an electrically conductive medium, the rise time of an electronic pulse traveling in a wave guide degrades because conductivity losses. DeHart in U.S. Pat. No. 6,798,215 taught a method of computing the amount of degradation and mathematically computing a correcting the propagation calculations based on determine the slope of the rising edge of the incoming wave. Anderson in Pub. No. US 2003/0042916 A1 teaches an alternative method of computing the amount of degradation and mathematically correcting the propagation velocity based on using a high speed latching comparator to sample the wave at a number of amplitudes. These samples effectively digitize the wave. The point of inflection marking the arrival of the incoming wave can be computed from the digitized wave. Anderson continues to refine and broaden this sampling technique in publications Pub. No. US 2004/0164750 A1, Pub. No. US 2004/0164746 A1 and Pub. No. US 2004/0059509 A1. While these methods are precise, they are typically complex and can be somewhat costly.

This invention provides a method where the propagation time or velocity of the wave can be found in a way that is independent of the rise time of the incoming wave. This invention significantly extends the current state of the art by simplifying the detection the leading edge of the incoming wave. The incoming wave is differentiated to determine the point of inflection marking the arrival of the transmitted wave.

This invention also provides a method to compute a measure of the amount of degradation of the wave, therefore inferring the amount of conductive material in the medium. Conductivity in soils is a marker for high ion content caused by salts and fertilizer. A high level of salts can cause changes in the preferred watering profiles. High levels of salt may also necessitate a remediation plan.

DETAILED DESCRIPTION OF THE PREFERRED EMBODIMENT

Figure 1:
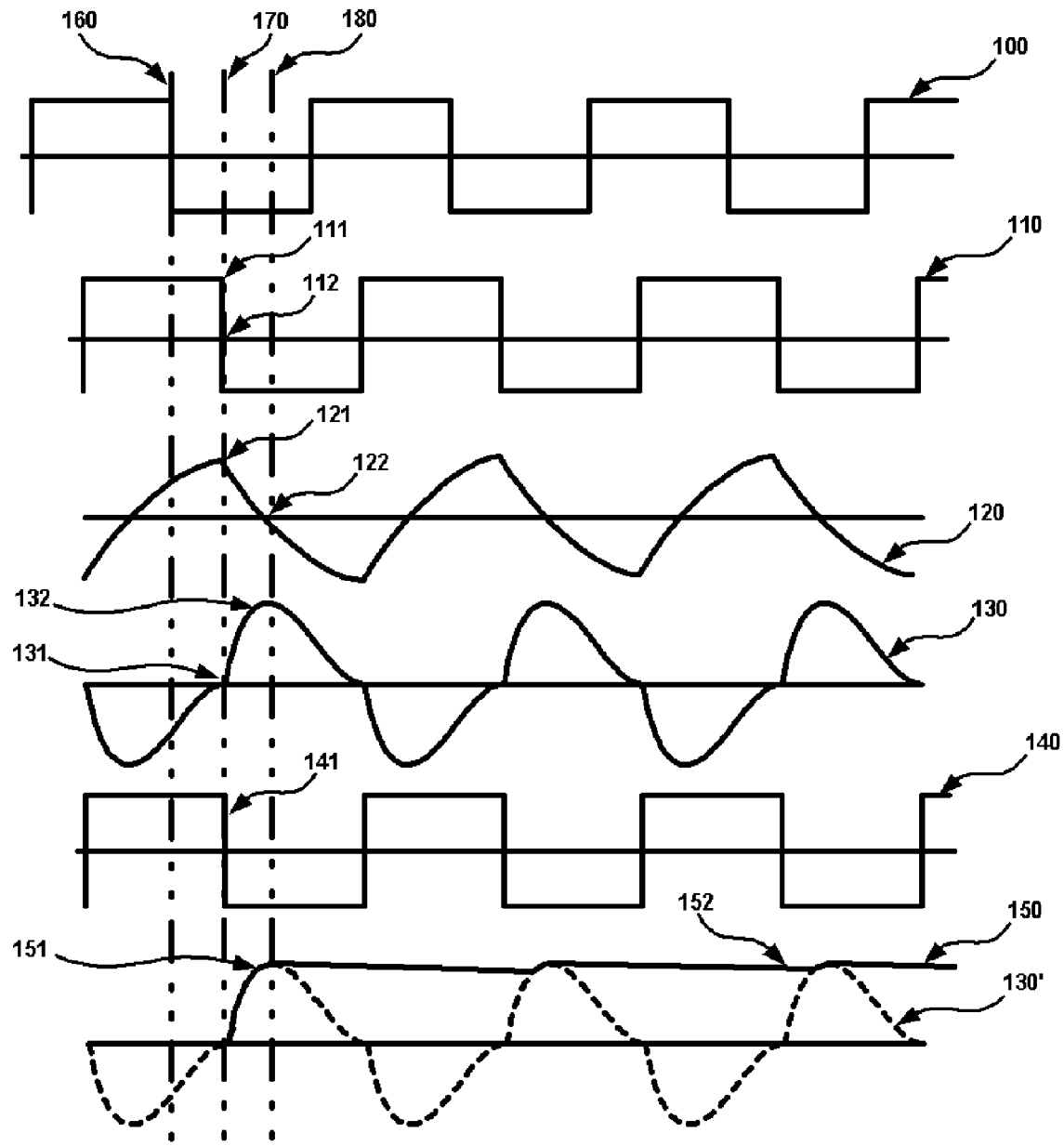
FIG. 1 is a diagram showing six time based wave forms. The first wave 100 represents a transmitted wave. The second wave 110 represents an ideal received wave with no degradation. The third wave 120 represents an actual received wave with degradation. The fourth wave 130 represents the wave after it is differentiated with its zero crossing points corresponding to the points of inflection 121 of the received wave. The fifth wave 140 represents the output of the comparator that toggles based on the polarity of the differentiated signal. This signal represents the true delay of the signal. The sixth wave 150 is the output of a circuit capturing the maximum value of the differentiated. The amplitude of this signal is inversely proportional to the signal loss.

FIG. 1 demonstrates the propagation delay of a wave traveling through a medium of similar dielectric constant but with differing conductivity. FIG. 1 contains six time-based waveforms and is useful to illustrate the problem addressed by the present invention. The first wave 100 from the top represents an ideal transmitted wave. The next two waves, 110 and 120, represent the received waves after the transmitted wave has been transmitted through the medium to be measured. The second wave 110 represents an ideal received wave. The third wave 120 illustrates a typical received wave in a medium with moderate conductivity. The slow rise and fall times of the second wave 120 illustrates signal degradation due to conductivity losses.

The dielectric constant is estimated by determining the delay between the transmitted wave and the ideal received wave. Thus, if one can accurately determine the timing of the edges of the ideal received wave, one can accurately estimate the dielectric constant. However, due to limitations in inexpensive electronics used to process the signal, the received wave voltage cannot be measured directly to provide an accurate reading of the point of inflection of the received wave. Note that in the ideal case 110 the time difference between the arrival of the wave 111 and the point were it crosses the comparator trigger point 112 is very small. In the non-ideal case 120 the difference between the point of inflection reached at the arrival of the wave 121 and the point where the amplitude crosses the trigger point 122 is significant. This represents error and is significant in a conductive medium.

The present invention solves this problem by accurately determining the point of inflection 121 in the received wave by differentiating the received wave. The output of the differentiator will approach zero 131 as the point of inflection is approached. After the point of inflection is reached, the received signal moves rapidly in with opposite polarity as is demonstrated between points 121 and 122. The fourth wave 130 demonstrates the output of the differentiator when it differentiates the third waveform. The differentiator will move to a high voltage output 132 proportional to the maximum slope of the received wave. The differentiated signal has sharp edges that can be detected with a high-speed comparator. The fifth wave 140 represents the output of the comparator. Note that the comparator output matches the ideal wave 110. The process of differentiation before the comparator effectively neutralized the effects of the conductive medium.

The maximum amplitude 132 of the differentiated signal 130 is proportional to the rise time of the received wave. The maximum amplitude detector measures the peak amplitude of the differentiated voltage 151 and thus is an indication of the signal degradation. This parameter can be used as a second order correction factor when measuring the dielectric constant or output directly as a measure of the conductivity.

Figure 2:
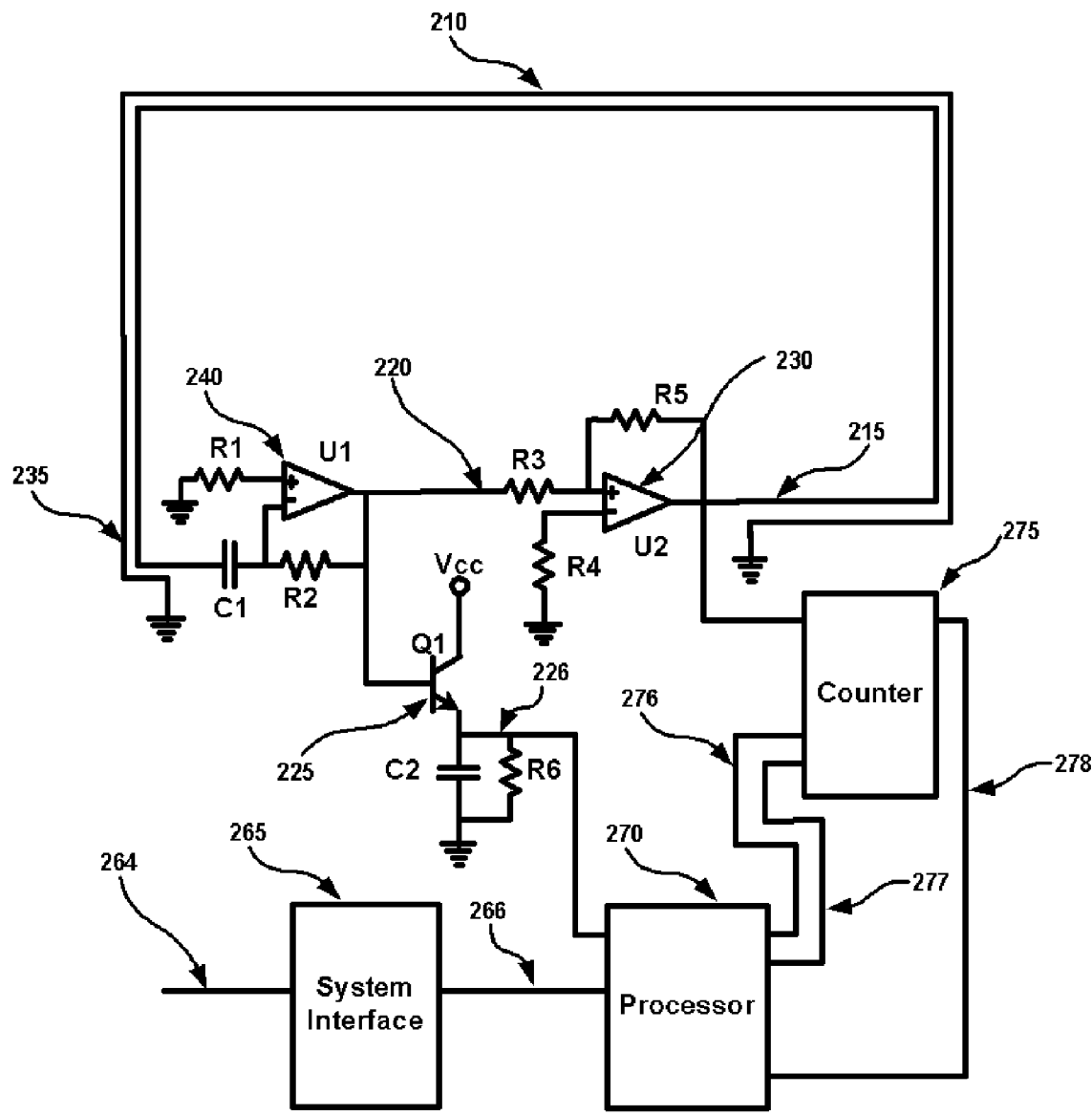
FIG. 2 is a block diagram of the preferred embodiment wherein the transmitted wave is transmitted down a transmission line 210. The transmission line is placed in the medium of interest. The propagation time down the transmission line is a function of the characteristic impedance of the transmission line. The characteristic impedance is a function of the dielectric constant of the medium. The circuitry is designed such that as each wave reaches the end of the transmission line 235, another wave is launched down the transmission line 215 causing a variable frequency that provides a useful estimate of the dielectric constant of the material. The output of the maximum amplitude capturing circuit 225 provides a method to determine the amount of conductivity material. The counter 275 counts the number of cycles in a period of time. An analog to digital converter in the processor 270 reads the maximum amplitude 226. The processor 270 calculates the dielectric constant based on the number of cycles in a specific. The processor communicates the desired information through the system interface function 265.

FIG. 2 is a block diagram of a system implementing the correction method for processing the waves illustrated in FIG. 1. It is helpful to understand how the waves of FIG. 1 are presented to the system of FIG. 2. Referring to both FIG. 1 and FIG. 2, the transmitted wave, the first wave 100, is the voltage at the sending end 215 of the transmission line 210 of FIG. 2. The ideal received wave, the second wave 110 shows the ideal wave as it arrives at the receiving end 235 where the impedance of the transmission line 210 matched producing an exact replica of the original wave 100, but delayed in time. The received wave with moderate conductivity, the third wave 130, shows the wave as it arrives at the receiving end 235 of the transmission line 210 of FIG. 2 in a medium with moderate conductivity.

In the moderately conductive medium, there is a definite rise and fall time associated with this wave 120. Also note that the time it takes from launching of the transmitted wave to the zero crossing point 122 is definitely longer than the time to the zero crossing point 112 on the ideal received wave. The edge of the received wave corresponds to the point of inflection 121. It is important to note that with moderate conductivity of inflection 121 arrives at the same time as the ideal wave 111, but the fall time is significantly longer. The detection method senses this point of inflection, of the received wave, 111 and 121 at point 235, by differentiating the incoming wave producing output 130 at point 220. Note that the differentiator output 130 at point 220 crosses the zero crossing 135 at the point of inflection of the incoming wave 111 and 121. The comparator 230 will output a positive voltage when the input 220 is a positive voltage and will put out a negative voltage when the input 220 is a positive voltage. The comparator 230 changes state as the input 130 at point 220 changes polarity producing the output 140 at point 215. The output 140 of the comparator 230 changes state at the same time as the ideal wave 110. The effects of the signal degradation caused by conductivity losses have been effectively cancelled out.

Figure 3:
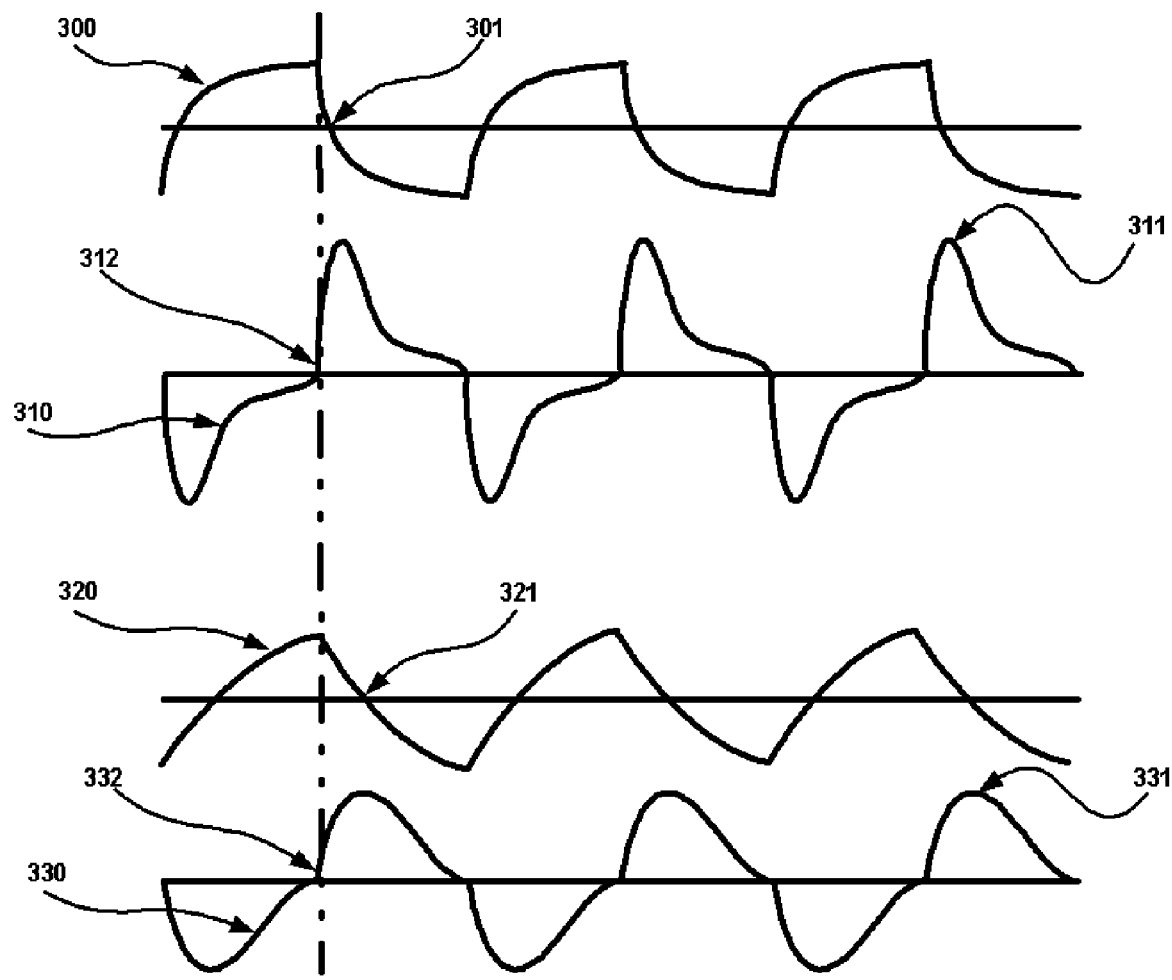
FIG. 3 shows a comparison of a received wave 300 in a slightly conductive environment with the differentiated waveform 310 and the received wave 320 in a more conductive environment with the differentiated waveform 330.

FIG. 3 compares the performance of the technology in two samples with different conductivity. FIG. 3 shows a comparison of a received wave 300 in a slightly conductive environment and its associated differentiated wave form 310 with the received wave 320 in a more conductive environment and its associated differentiated wave form 330. Note that the amplitude 311 of the differentiated waveform 310 of the less conductive is greater than the amplitude 331 of the differentiated waveform 330. This greater amplitude is a result of the faster rise time of the received wave 300. This change of amplitude of the differentiated wave 311 and 331 is proportional to conductivity losses in the medium.

The comparator will trigger at points 312 and 332. Points 312 and 332 have very little time shift when compared to the time shift that would have been produced if the comparator triggered on the zero crossing points of the received waves 301 and 321. The time shift between 301 and 321 is very significant and represents error in the propagation delay measurement. These curves 310 and 330 graphically demonstrate the results of using differentiation to find the arrival of the wave down the transmission line the allowing the true propagation delay to be easily determined even though the received waves 300 and 320 have very different characteristic shapes.

FIG. 2 further illustrates a sensor apparatus composed of the following:

(1) A high speed analog differentiator 240

(2) A high speed comparator and line driver 230

(3) A maximum value capture circuit 225

(4) A transmission line 210

(5) A counter 275

(6) A control section composed of a microprocessor 270 with integrated analog to digital converter (7) A system interface 265.

The high-speed analog differentiator 240 consists of U1, R1, R2 and C1. A change of voltage at the input to the differentiator 235 causes a voltage change across capacitor C1 which intern causes a current to flow through C1 The relationship is defined by $$I_{cap} = C1 * dV/dT$$

Where I is the current through the capacitor, C1 is the value of the capacitor, dV is the change in voltage across the capacitor and dT is the amount of time over which the change in voltage occurred. Basic operational amplifier design, U2, dictates that the current through resistor R2 is equal to the current $I_{cap}$. The Differentiator output voltage 220 is defined as:

$$V_{out} = -I_{cap} * R2 = -C1 * dV/dT$$

$V_{out}$ 220 is the output of the differentiator 240. $V_{out}$ is the derivative of the voltage at the input 235 because the circuit performs the basic differentiation function of producing an output that is proportional the instantaneous change in the input voltage. In practice, a large value resistor is added in parallel with C1 This resistor provides the low frequency gain to initialize the system and assure startup. The value should be such that the current through the resistor is small compared the current through C1 when the circuit is running at speed.

The high-speed comparator 230 consists of U2, R3, R4, and R5. R4 provides the reference for the switch point while R3 and R5 provide positive feedback providing noise rejection with crisp edges.

An idealized maximum value capture circuit 225 is illustrated by Q1, R6 and C2. As the differentiator output voltage 220 rises, the Q2 will conduct causing the voltage 226 across C2 to rise. When the differentiator output voltage drops, the base emitter junction will reverse bias and no current will flow. The voltage across the capacitor therefore retains the peak amplitude of the differentiator output voltage 220. R6 provides a discharge path that will eventually return the voltage across C2 to zero. The value of R6 is chosen such that the RC time constant of R6 and C2 is long compared to the time period of interest. This process is demonstrated in FIG. 1 trace 150. The trace at 151 demonstrates a portion of the cycle where Q1 is conducting and the voltage across the capacitor is following the input voltage 220. The trace at 152 demonstrates the portion of the cycle where the base emitter junction is reversed bias and the current flowing through R6 is reducing the charge across C1.

The output voltage of the differentiator 220 will go negative. When the differentiator voltage goes negative, the positive input to comparator 230 will go negative with respect to the negative input which in turn will cause the output 215 to go negative. The negative edge will now be transmitted down the transmission line 210. When it reaches the end of the transmission line 235 the voltage at 235 stops rising and starts going negative defining a point of inflection where there is no slope and dV/dT=0. The output of the differentiator 220 will equal 0 volts immediately followed by a rapidly rising positive edge. The comparator switches just as the differentiator begins to move to a positive voltage. This process continues to indefinitely with the time between transitions equal to the propagation time of the delay line.

A reading is initiated by a command arriving at the system interface 265 and presented to the processor 270. The processor 270 exerts the clear line 276 on the counter. The processor 270 will then enable the counter 275 by asserting enable line 277. Counter 275 will begin counting each time a positive edge is generated by the comparator 230. The processor will assert the enable line 277 for a precise period of time and then de-assert the enable line 277. The processor 270 will then read the total count through counter interface 278. The processor 270 will also read the amplitude 226. With this information the processor can determine the total distance traveled by the wave over the precisely timed period the counter 275 was enabled.

The preceding embodiment discussed using a conventional delay line where a signal is imposed on the sending end of the transmission and the signal is picked up on the receiving end of the transmission line. Using a differentiator to determine the precise arrival of a received wave is equally applicable when used with time-domain reflectometry. A time-domain reflectometry system a wave is transmitted on the transmission line. The wave propagates to the open end of the transmission and is reflected back to the sending end of the transmission line. The reflected wave is coupled into the receiver. The transmission time is the time that it takes for the wave to propagate to the open end of the transmission and back.

The disclosed technology is equally applicable to differential transmission line where both lines are energized with signals of opposite polarity.

By knowing the total distance traveled by the wave in the give period the dielectric constant can be calculated. By knowing the number of times that the wave traversed the wave guide and subtracting out the electronic delay time and correcting for the conductivity of the medium, the total distance traveled by the wave in the sample time can be calculated. The distance traveled per unit of time is the propagation velocity. The following formula gives the relationship between propagation velocity (V) and the bulk dielectric constant (k). C is the speed of light.

$V = C/k^{0.5}$

Solving for k $k = (C/V)^2$

The moisture content can then be determined based on the dielectric constant.

What is claimed is:

1. A system for monitoring material having an associated dielectric constant in an environment wherein the material exhibits conductivity comprising:
   a transmission line wherein the transmission line is surrounded by the material and an electrical signal is propagated through the transmission line,
   a received waveform wherein the received waveform is derived from the electrical signal after the electrical signal has propagated through the transmission line,
   a differentiator which differentiates the received wave creating a non-zero output amplitude proportional to the rise time of the received wave,
   an amplitude capture circuit where the amplitude of the differentiated received signal is captured,
   wherein an ideal signal is computed which reflects the dielectric constant in an environment free from conductivity,
   wherein the material exhibits conductivity wherein the amplitude of the differentiated signal represents the degradation of the received signal from the ideal signal, and the degradation is interpreted as an approximation of the conductivity of the material and is monitored,
   wherein the amplitude of the differentiated signal is used as a second order correction factor to correct said approximation of the conductivity.

2. The system of claim 1 wherein the electrical signal is a differential electrical signal.

3. The system of claim 1 wherein the environment is an irrigation environment.

* * * * *